United States Patent [19]

Wadsworth

[11] Patent Number: 5,188,637
[45] Date of Patent: Feb. 23, 1993

[54] CLIP FOR ELASTOMERIC LIGATION TUBING

[76] Inventor: Legrand D. Wadsworth, Rt. #1, Box 168, St. Ignatius, Mont. 59865

[21] Appl. No.: 886,141

[22] Filed: May 21, 1992

[51] Int. Cl.⁵ .................................... A61B 17/00
[52] U.S. Cl. .................................... 606/151; 606/135; 24/129 R; 24/129 B; 24/129 W; 24/563
[58] Field of Search ............... 606/135, 151, 157, 158; 24/115 R, 129 R, 339, 563 X, 129 B, 129 W; 403/210, 212, 398, 405.1

[56] References Cited

U.S. PATENT DOCUMENTS

| | | | |
|---|---|---|---|
| 344,567 | 6/1986 | Coleman | 248/229 |
| 646,091 | 3/1900 | Hammond | 24/129 B |
| 1,550,900 | 8/1925 | Goodspeed | 403/210 |
| 2,326,100 | 8/1943 | Lavarack et al. | 439/868 |
| 4,080,157 | 3/1978 | Albertson, et al. | 24/370 |
| 4,217,902 | 8/1980 | March | 606/221 |
| 4,691,704 | 9/1987 | Wadsworth | 606/135 |
| 4,735,615 | 4/1988 | Uddo, Jr. et al. | 606/151 |
| 4,826,114 | 5/1989 | Umehara | 24/563 |
| 4,869,268 | 9/1989 | Yoon | 606/135 |
| 4,928,634 | 5/1990 | Voigt | 24/129 R |

*Primary Examiner*—Stephen C. Pellegrino
*Assistant Examiner*—Gary Jackson
*Attorney, Agent, or Firm*—Keith S. Bergman

[57] ABSTRACT

A metallic clip, to fasten two ends of latex surgical tubing under tension when used as a ligation element especially as in the castration of animals, provides a cylindrical tubular element defining an axially aligned slit through its periphery, with each side portion adjacent the slit defining angulated slots extending spacedly inwardly from a first end of the clip in a diverging fashion, to receive tubing ends. The clip defines an outwardly extending alignment protuberance inwardly from the second end of the clip in a position diametrically opposed to the peripheral slit. For use two latex surgical tubes are passed through the clip channel and one end portion of the tube is inserted in each slot. After tensioning the tubing, the clip is mechanically deformed, preferably by a tool created for such purpose, to bend each body portion between the slot and the slit inwardly to fasten each adjacent tube portion between that clip portion and the opposite side wall of the clip.

4 Claims, 1 Drawing Sheet

U.S. Patent  Feb. 23, 1993  5,188,637
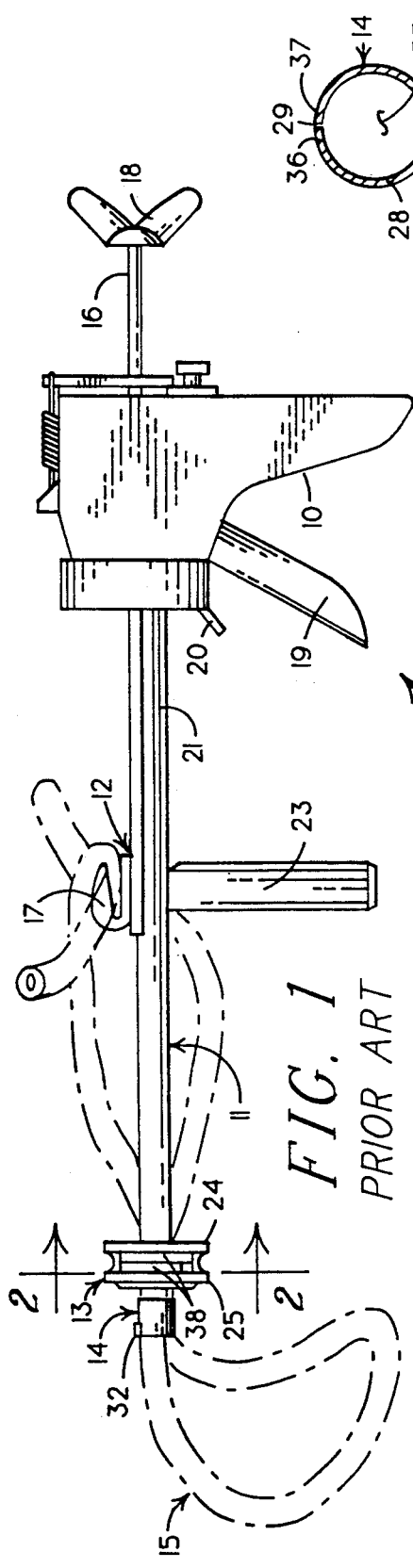

CLIP FOR ELASTOMERIC LIGATION TUBING

BACKGROUND OF INVENTION

A. Related Applications

There are no applications related hereto heretofore filed in this or any foreign country.

B. Field of the Invention

This invention relates generally to surgical devices and more particularly to a tubular clip that is deformed to fasten adjacent portions of tensioned elastomeric ligation tubing in a permanent fashion.

C. Description of Prior Art

In the practice of animal husbandry and surgery, ligation has long been known to cause the atrophy of body parts outwardly of a ligation site. Such areas, when cut off from systemic control and supply, atrophy quite readily and the ligation site generally heals effectively by the time of atrophy.

The ligation process is well suited to castration of animals having testicles carried in an external scrotal pouch, such as bovines, horses, goats and sheep. The process is bloodless and requires no opening or exposure of body tissues or cavities, to alleviate many of the problems associated with ordinary surgical procedures such as bleeding, microbal invasion, insect infestation. The ligation castration process is commonly applied differently with different animals, with endless elastomeric bands commonly being used with smaller animals and bands of selectable length, formed by fastening the looped ends of latex surgical tubing together, with larger animals. A process of the latter type and a tool for use in such a process was disclosed in U.S. Pat. No. 4,691,704 issued Sep. 8, 1987 to the instant inventor.

When latex surgical tubing is used in ligation castration, that tubing is subject to substantial tensive force. A clip that holds the two ends of the ligation material must resist and accommodate this force without damaging the tubing at the connection site to be effective. The problem of interconnecting the ends of ligation tubing is further enhanced by the fact that the tubing must remain in substantially its original tensive condition during the atrophy process of some two or three weeks or more, and during this time, the ligation material is being carried by a living, moving animal which may subject the ligation site to various disruptive external forces and conditions. The results of such conditions on ligation clips is further accelerated by the elastic and resilient deformability of the latex tubing which aid tubing motion relative to a rigid clamping structure.

Ligation castration, however, requires a very secure and permanent fastening of the ends of elastomeric ligation material. If that fastening is not secure, the material may loosen and then not only fail to accomplish its purpose, but also cause secondary problems that may effect an animal's health or even its life. The instant invention seeks to provide a new and novel clip for such ligation process that provides the requisite fastening of elastomeric surgical tubing.

Various methods of fastening together the ends of a band of elastomeric ligation material have heretofore become known and used. Tying or knotting is commonly used by surgeons but is not particularly effective firstly, because it is difficult to fasten the ends of elastomeric tubing together when they are under substantial tension, and secondly, because such fastening in elastomeric material is not particularly permanent and tends to allow relative motion of fastened portions responsive to changing forces, often to allow reduction of tension in ligation material or even its displacement or removal. Knotting or tying also tends to provide a connection that has substantially less strength in the connection area than the strength of the tubing being interconnected.

Clips that have become known for fastening elastomeric ligation materials have generally provided a deformable metallic structure of an annular or cylindrical nature defining a channel through which portions of tubing to be joined are passed, with some adjacent deformable clip portion to fasten the tubing within the clip channel. After fastening deformation of such clips, generally clip portions and both portions of the tubing are in surface adjacency with each other, so that one tube may move relative to the other and either tube may move relative to the clip. Such an annular grommet-like device was disclosed in the aforesaid U.S. Pat. No. 4,691,704. This type of clip in general is operative to fasten elastomeric ligation tubing, but on occasion, depending especially upon its manner of use, the clip may not completely and securely interconnect the ends of ligation tubing and may allow some motion of the interconnected portions.

The instant invention seeks to alleviate this problem by providing a clip that fastens each tube end portion independently within the clip structure and does not allow or depend upon adjacency of any portions of the two tubes for its connecting junction. The clip further does not provide any type of completely enclosing annular structure so that its two side portions may be bent upon each individual tubing portion being fastened. This provides a substantially greater fastening area between tube and clip than is provided by a traditional clip having annular structure defining a completely closed periphery that extends about the tubes, while yet maintaining an axial length of the clip within reasonable and desirable limits. My improved clip differs from clips heretofore used with elastomeric ligation tubing in these aspects.

SUMMARY OF INVENTION

My clip provides a peripherally defined, metallic tubular element having an internal channel to receive the end portions of two elastomeric surgical tubes to be connected. The clip defines a slit in its peripheral surface extending in axial alignment between its opposed ends. Two slots are defined in the clip to extend from a first clip end, in divergent angulated orientation to each other and to the slit, to a spaced distance from the second end. The clip defines an indexing protuberance adjacent its second end in a position diametrically opposed to the slit.

In use, the ends of ligation tubing to be interconnected are inserted through the clip channel and positioned in one of the slots defined in the clip. After tensioning the tubing, each clip portion between the slit and a slot is bent inwardly against the tubing in the associated slot to cause a fastening of the tubing in the clip. This clip deformation may be accomplished by use of a specialized tool created specifically for the purpose, such as that disclosed in U.S. Pat. No. 4,691,704.

In creating such a clip, it is:

A principal object to provide a clip that securely fastens two adjacent portions of elastomeric ligation tubing in a secure fashion that prevents motion of the fastened elements, when subjected to substantial tensive forces and irregular external forces, to prevent loosening or lessening of tension in a ligation band.

A further object is to provide such a clip that fastens each tubing portion between clip portions by deformable interconnection of one clip portion, without either tubing portion having any fastening contact with the other.

A still further object is to provide such a clip that is easily deformable by use of existing tools, and especially by known specialized tools for ligation castration of larger animals.

A still further object is to provide such a device that has an indexing protuberance that allows the annular clip to be inserted in an encompassing chamber of a deforming tool in only one particular orientation, so that the deforming process may be uniformly and properly carried out by that tool.

A still further object is to provide such a device that is of new and novel design, of rugged and durable nature, of simple and economic manufacture and operation and otherwise well suited to the uses and purposes for which it is intended.

Other and further objects of my clip will appear from the following specification and accompanying drawings which form a part hereof. In carrying out the objects of my invention, however, it is to be understood that its essential features are susceptible of changes in design and structural arrangement, with only one preferred and practical embodiment of the best known mode being illustrated in the accompanying drawings and specified, as is required.

BRIEF DESCRIPTION OF DRAWINGS

In the accompanying drawings which form a part hereof and wherein like numbers of reference refer to similar parts throughout:

FIG. 1 is a side view of a tool of the prior art commonly used for tightening elastomeric ligation tubing and deforming a metallic clip to fasten the end portions of that tubing.

FIG. 2 is a vertical cross-sectional view through the device of FIG. 1, taken on the line 2—2 on that Figure in the direction indicated by the arrows thereon.

FIGS. 3, 4, 5 and 6 are isometric views showing progressive stages in the formation process of my clip.

FIG. 7 is a vertical cross-sectional view through the form clip of FIG. 6 taken on the line 7—7 in the direction indicated by the arrows thereon.

FIG. 8 is a somewhat enlarged isometric view of the clip of FIG. 6 deformed to fasten two portions of elastomeric ligation tubing.

DESCRIPTION OF THE PREFERRED EMBODIMENT

A tool disclosed in U.S. Pat. No. 4,691,704 that is used for the formation of ligation loops in elastomeric surgical tubing to castrate animals is illustrated in FIGS. 1 and 2. The tool provides handle 10 carrying elongate forwardly extending body 11, the forward portion of which carries clip 14 through which ligation tubing 15 is passed in a loop so that its end portions may be carried by tensioning element 16 and moved rearwardly by associated mechanism carried by the handle to create tension in the tubing. The clip 14 is carried in crimping chamber 13, defined in the forward portion of body 11 to interconnect the ends of the ligation material in a tensioned condition at that point.

Handle 10 carries tensioning member 12, in the instance illustrated providing elongate rod 16 carrying the ends of looped ligation material 15 in wedge-type fastening structure 17 defined in its forward part. Slack may be removed from the ligation material by manually moving rod 16 rearwardly by use of end wing structure 18 and the rod then may be mechanically tightened by operating trigger 19 which is operatively engaged by means of trigger lever 20. Various other mechanical means are known to accomplish the same purpose, and the action may be motorized if desired. Most similar devices may be used with my clip.

Body 11 provides two similar elongate side-by-side tubes 21, each pivotally supporting in its medial channel a crimping axle 22 that may be pivoted relative to the tube by manually moving irrotatively connected crimping rod handles 23. the forward portion of tubes 21 support rearward crimping plate 24 and spacedly adjacent forward crimping plate 25. Each crimping plate defines a medial clip orifice 26 to receive and positionally maintain clip 14. The clip orifice defined in forward clip plate 25 further defines an indexing notch 27 extending radially outwardly from the orifice to receive an indexing protuberance of a clip for positional orientation. Each crimping rod 22 extends into the space between forward and rearward crimping plates and there irrotatively carries a crimping dog 38 which is spacedly related in a forward-rearward direction relative to the crimping dog of the other crimping rod to allow independent simultaneous pivoting of both dogs. It is also possible, and often even desirable, to crimp a clip such as disclosed by the instant invention in a device such as described that has only a single crimping dog of appropriate shape.

The clip of the instant invention is quite effectively useful with such structure, though it may also be used with other similar known types of crimping tools and with other crimping devices.

My clip provides a cylindrical deformable structure illustrated particularly in the isometric view in FIG. 6 and in FIG. 7. Clip 14 provides peripherally defined cylindrical body 28 with slit 29 extending in an axially aligned position between opposed ends 30 and 31. Slit 29 is of relatively narrow width, generally not more than 0.05 inch (0.1127 cm.). Indexing protuberance 32 extends spacedly from end 30 in an axially aligned orientation and a position that is diametrically opposed to slit 29. The size and configuration of indexing protuberance 32 is not particularly critical. In the instance illustrated, the protuberance has a width perpendicular the axis of the clip cylinder approximating 0.1 inch (0.254 cm) and a length extending inwardly from end 30 a distance less than one-third of the clip body length or approximately 0.3 inch (0.762 cm). This indexing protuberance need only have sufficient size to provide appropriate radial indexing of a clip in the crimping orifice 26 of a crimping tool, and any excessive size beyond that required merely necessitates larger structures that are not desirable.

Tubing slots 33 are defined in cylindrical body 28 spacedly adjacent each side of slit 29, each slot extending from end 31 in an angulated orientation away from the slit. These slots extend to a spaced distance from end 30 and terminate in a curvilinear end portion 34 which will accept, but will not cut or structurally damage, ligation tubing carried therein. The width of the slots is substantially the same as the relaxed diameter of ligation tubing to be fastened within the clip.

My clip structure is preferably formed from sheet aluminum material of a thickness approximating 0.05 inch (0.1127 cm). Other metals will serve to form clips, but the deformability and ability to retain a deformed crimped configuration are both well served by aluminum. My clip is preferably formed by a die stamping process as illustrated in FIG. 3 through 6. A blank of appropriate configuration is firstly stamped from flat sheet material and, as illustrated in FIG. 3, indexing protuberance 32 is stamped into the blank and slots 33 are defined. Thereafter, as illustrated in FIG. 4, a medial portion of the blank is formed substantially to its circular configuration. As illustrated in FIG. 5, the side portions of the clip are then formed to their cylindrical configuration, and thereafter the entire clip structure is formed about an arbor to produce the finished clip illustrated in FIG. 6.

The use of my clip can be understood, especially with reference to FIG. 8 and the prior art diagrams of FIGS. 1 and 2.

As seen in FIG. 1, two ends of ligation tubing 15 are passed through channel 35 defined by my clip and positioned in the clip where it be desired that they be fastened. The two tubes are aligned in adjacency, with a line through their centers being substantially perpendicular to a line passing through slit 29 and the medial portion of indexing protuberance 32. The end portions of the ligation tubing are then placed in adjacent tubing slots 33 which tends to align the portion of the tubes within the clip in the proper orientation specified. With the clip in this condition, the portion 36 of the clip body adjacent one side of slit 29 is moved inwardly within what formerly was channel 35, and this deformation is continued until the portions 36 is substantially adjacent the diametrically opposed portion of the clip body, as illustrated in FIG. 8. The body portion 37 of the clip adjacent the other side of slit 29 is moved in similar fashion over and about the other tube portion within the clip to fasten it. Both fastening operations may be accomplished simultaneously if desired.

The fastening described may be accomplished with various tools that aid clip deformation, but in general with the ligation tubing under tension when it is to be fastened, some specialized tool is required to maintain the tension while accomplishing the deformation process. To use the tool illustrated in FIGS. 1 and 2, end portions of ligation tubing 15 are passed through channel 35 defined by my clip and each end portion is established in one tubing slot 33 of the clip. The end portions of the tubing are then passed through crimping orifice 26 defined in the tool and thence rearwardly along tool body 11 to fastening structure 17 where they are fastened in the wedge-like channels defined by that element. The clip is then positioned in crimping orifice 26 where it is partially contained by the crimping plates defining that orifice. The indexing protuberance 32 of the clip is positioned in indexing orifice 27 defined at least in the forward crimping plate 14, which not only maintains the clip in proper radial orientation but also prevents it from moving rearwardly through the crimping chamber since the crimping is defined only the forward crimping plate 25.

To insert a clip in crimping chamber 26 of the device illustrated, the crimping dogs 38 are pivoted so that their outer end portions are outside crimping channel 26 to be occupied by the clip. This is accomplished by moving crimping rod handles 23 in a pivotally fashion away from each other. After the clip is inserted in the crimping chamber, the crimping dogs will be maintained in this orientation by reason of the presence of the clip.

With the tool in this condition, a portion of the ligation loop extending forwardly of the clip is placed about the scrotal pouch of an animal, immediately adjacent its interconnection with the animal's body, and the ligation tubing is tightened by operation of trigger 19 to create the desired tension in the ligation loop. When this tension has been attained, the two crimping rod handles 23 are moved pivotally inwardly toward each other and as this occurs, the outer end portions of crimping dogs 38 will engage body portions 36 and 37 of the clip. As the motion is continued, the crimping dogs will move the portions 36, 37 of the clip into the fastened configuration illustrated in FIG. 8. substantially adjacent the opposite clip wall. After the clip is thusly crimped to fasten the ligation tubing, tension maintained by the tensioning tool is released, the tool is removed from the clip and tubing and the ends of the tubing are trimmed outwardly of the then fastened clip.

It is to be particularly noted that the clip structure will extend about each portion of fastened tubing over a substantial area, but yet no portion of either tube is in communication with the other to make the fastening more secure. Grommet type clamps which maintain portions of each end of the ligation tubing in contact with each other to form part of the interconnecting structure have more tendency for the adjacent tubing portions to move relative to the clamp and relative to each other then does my instant clip, where each connected tube is separately and individually fastened by only the clamping structure itself.

The foregoing description of my invention is necessarily of a detailed nature so that a specific embodiment of it might be set forth as required, but it is to be understood that various modifications of detail, rearrangement and multiplication of parts might be resorted to without departing from its spirit, essence or scope.

Having thusly described my invention, what 1 desire to protect by Letters Patent, and

What I claim is:

1. A deformable clip to fasten two adjacent portions of elastic ligation tubing thereon, comprising in combination, a peripherally defined tubular body having first and second ends and an internal channel to accept two portions of ligation tubing in side-by-side relationship, said body further having an elongate slit defined through the body and extending from the first end to the second end, indexing means to determine the rotary position of the body relative to a deforming tool and slots, spacedly distant from the slit and on each side thereof to hold tubing and aid the deformation of each body portion between the slot and the slit to a position substantially adjacent the opposed body portion on the same side of a diameter through the slit.

2. A clip to fasten two adjacent portions of elastic ligation tubing thereon, comprising in combination:

a peripherally defined, deformable tubular body having first and second ends and an internal channel to allows side-by-side passage of two portions of ligation tubing therethrough, said body having an axially aligned slit extending through the body from the first end to the second end;

an indexing protuberance extending outwardly from the body adjacent the first end and diametrically opposite the slit, and two similar tubing slots defined in the body, each said slot extending inwardly a spaced distance from the second end from the points on either side of the slit and spacedly distant therefrom, said slots arrayed in angulated orientation away from the slit.

3. The clip of claim 2 further characterized by: the body being formed from sheet aluminum material having a thickness of substantially 0.050 inch, and the slots having a width not greater than the diameter of elastomeric ligation tubing to be fastened by the clip.

4. The clip of claim 2 fastening two portions of elastomeric ligation tubing therein, one portion of said tubing fastened by each body portion between the slot and the slit with the said body portion deformed inwardly toward the opposed portion of the clamp on the same side of a diameter through the slit.

* * * * *